United States Patent [19]
Jones et al.

[11] Patent Number: 6,126,920
[45] Date of Patent: Oct. 3, 2000

[54] METHOD OF TREATING A SKIN DISEASE WITH A CORTICOSTEROID-CONTAINING PHARMACEUTICAL COMPOSITION

[75] Inventors: Julie Irene Jones, Herpenden; Anthony Richard Baker, West Horsley, both of United Kingdom; Neil Graham Halls, Glen Waverley, Australia; Peter Watmough; Peter Marriott, both of Grimsby, United Kingdom

[73] Assignee: Medeva Europe PLC, London, United Kingdom

[21] Appl. No.: 08/913,144

[22] PCT Filed: Mar. 1, 1996

[86] PCT No.: PCT/GB96/00490

§ 371 Date: Jan. 12, 1998

§ 102(e) Date: Jan. 12, 1998

[87] PCT Pub. No.: WO96/27376

PCT Pub. Date: Sep. 12, 1996

[30] Foreign Application Priority Data

Mar. 3, 1995 [GB] United Kingdom .................. 9504265

[51] Int. Cl.⁷ ....................................................... A61K 7/48
[52] U.S. Cl. ............................................. 424/45; 514/945
[58] Field of Search ................................. 424/45; 514/945

[56] References Cited

U.S. PATENT DOCUMENTS 4,018,918   4/1977   Ayer et al. .

FOREIGN PATENT DOCUMENTS

0423695A3   4/1991   European Pat. Off. .
0484530A1   5/1992   European Pat. Off. .
85/01876    5/1985   WIPO .

OTHER PUBLICATIONS

Yip and Po "The stability of betamethasone–17–valerate in semi–solid bases" *J. Pharm. Pharmacol.* 31, 400–402 (1979).

*Primary Examiner*—Thurman K. Page
*Assistant Examiner*—Alysia Berman
*Attorney, Agent, or Firm*—Heslin & Rothenberg, P.C.

[57] ABSTRACT

Methods of treating various skin diseases, and in particular, scalp psoriasis, utilizing a foamable pharmaceutical composition comprising a corticosteroid active substance, a quick-break foaming agent, a propellant and a buffering agent are disclosed. The quick-break foaming agent typically comprises an aliphatic alcohol, water, a fatty alcohol and a surface active agent.

15 Claims, No Drawings

6,126,920

METHOD OF TREATING A SKIN DISEASE WITH A CORTICOSTEROID-CONTAINING PHARMACEUTICAL COMPOSITION

CROSS REFERENCE TO RELATED APPLICATIONS

This application is a 35 U.S.C. §371 filing of PCT/GB96/00490, filed Mar. 1, 1996 which claims priority of GB 9504265.1, filed Mar. 3, 1995.

FIELD OF THE INVENTION

The present invention relates to an improved composition for the topical application of corticosteroid active substances to the skin of a subject.

BACKGROUND OF THE INVENTION

Corticosteroids, particularly in the form of the ester compounds, are used, inter alia, in the treatment of skin diseases in humans, such as eczema, infantile eczema, atopic dermatitis, dermatitis herpetiformis, contact dermatitis, seborrhoeic dermatitis, neurodermatitis, psoriasis and intertrigo. Formulations containing such active substances have conventionally been applied to the skin site in the form of alcoholic solutions, lotions or creams. However, there is a high degree of ineffectiveness with such formulations. Lotions and creams are generally too viscous to allow efficient penetration of the active substance to the epidermis, and solutions have a tendency to evaporate before penetrating the epidermis. In addition, conventional cream bases are irritating to the skin, particularly over the often long exposure that is required, and the fluidity of lotions often makes the physical application difficult to control. Moreover, it is necessary to rub such formulations into the target site to improve the penetration of the active substance into the epidermis, an action which itself produces irritation.

There has therefore been a very real need in the treatment of skin disorders requiring treatment with corticosteroids for improved formulations which target the most effective corticosteroid to the skin site with improved delivery of active, substance with decreased inconvenience and irritation, and increased ease of use for the patient.

The present invention provides an improved composition which addresses this need.

In one aspect, the present invention provides a foamable pharmaceutical composition comprising a corticosteroid active substance, a quick-break foaming agent, a propellant and a buffering agent.

Such a composition is applied to the skin site (after foaming) as a foam which is a thermophobic (heat sensitive) quick-break foam. On application to the skin, the composition is initially in the form of a mousse-like foam. The quick-break foam slowly breaks down at the skin temperature to a liquid to allow the alcohol and active substance to saturate the treatment site. Such a system provides enhanced penetration of the alcohol and active substance through the epidermis. Because the composition is supplied as a mousse, the semi-rigid behaviour of the composite makes it easier to handle and physically control. The foamed composition, when applied, provides a thick ball of foam which disintegrates easily when spread, allowing proper coverage of the skin site to be treated without premature evaporation of the solvent. It has been found important to include a buffering agent in the composition to stabilize the active isomer of the corticosteroid active substance in the complex foamable composition, otherwise the complex interactions within the foamable composition may result in the instability of the more active isomer.

DETAILED DESCRIPTION OF PREFERRED EMBODIMENTS

Use of a quick-break foaming agent is required in the present invention. Such agents are known. Suitable quick-break foaming agents in the present invention are those described in Australian Patent No. 463216 and International Patent Application WO 85/01876. It is generally preferred that the quick-breaking foaming agent comprises an aliphatic alcohol, water, a fatty alcohol and a surface active agent. Particularly preferred is a quick-break foaming agent having the following composition:

(a) an aliphatic alcohol, preferably in amounts of 40–90% w/w composition, more preferably 55–70% w/w, especially 57–59% w/w;

(b) water, preferably in amounts of 10–40% w/w;

(c) at least one fatty alcohol, preferably in amounts of 0.5–10% w/w; and (d) a surface active agent, preferably an ethoxylated sorbitan ester (as emulsifier), typically in amounts of 0.1–55% w/w.

In the quick-break foaming agent, the fatty alcohol may be chosen from, for example, cetyl, stearyl, lauryl, myristyl and palmityl alcohols and mixtures of two or more thereof. Mixtures of cetyl alcohol and a stearyl alcohol such as octadecan-1-ol have been found to be particularly preferred; the ratio between these two components may be adjusted to maintain foam viscosity throughout the broadest possible temperature range. In this situation, the stearyl alcohol maintains the viscosity at temperatures above 20° C. whilst cetyl alcohol maintains the viscosity below 20° C.

The aliphatic alcohol may preferably be chosen from methyl, ethyl, isopropyl and butyl alcohols, and mixtures of two or more thereof. Ethanol has been found to be particularly preferred.

Surface active agents utilised in the quick-break foaming agent may preferably be chosen from ethoxylated sorbitan stearate, palmitate, oleate, nonyl phenol ethoxylates and fatty alcohol ethoxylates, and mixtures of two or more thereof. Thus, for example, Polysorbate 60 (a mixture of partial stearic esters of sorbitol and its anhydrides copolymerised with approximately 20 moles of ethylene oxide for each mole of sorbitol and its anhydrides) has been found to be particularly preferred. The surface active agent enhances the fatty alcohol solubility in the system and enhances foam formation.

The propellant used may be chosen from conventional aerosol propellants. Thus, one may select the propellant from propane, butane, dichloro difluoro methane, dichloro tetrafluoro ethane, octafluoro cyclobutane, and mixtures of two or more thereof. It is necessary to select a propellant most compatible with the entire system. It is particularly preferred that the propellant be present in amounts preferably of 3–30% w/w, more preferably 3–10% w/w, especially 3–5% w/w. The maximum level of propellant will be determined as the amount miscible with the utilized water/aliphatic alcohol ratio. In addition to acting as a propellant, the propellant will also act as a solvent for the fatty acids and active substances in the aqueous/alcoholic system.

It is possible that other additives may be used. Thus, it is preferred to add a humectant to reduce the drying effects of the aqueous aliphatic alcohol. Such a humectant may preferably be present in an amount of 0.1–10.0% w/w, more preferably 0.5–3.0% w/w. It is particularly preferred that the humectant be propylene glycol, but other humectants such as glycerine, panthenol and sorbitol may be used.

The composition of the present invention may be used to deliver corticosteroid compounds which have utility in the topical treatment of skin disorders. Thus, for example, the composition of the present invention may be used to deliver the following topically-effective corticosteroids:

| | |
|---|---|
| alclometasone dipropionate | fluclorolone acetonide |
| amcinonide | fluocinolone acetonide |
| beclamethasone dipropionate | fluocinonide |
| betamethasone benzoate | fluocortin butyl |
| betamethasone dipropionate | fluocortolone preparations |
| betamethasone valerate | fluprednidene acetate |
| budesonide | flurandrenolone |
| clobetasol propionate | halcinonide |
| clobetasone butyrate | hydrocortisone |
| desonide | hydrocortisone acetate |
| desoxymethasone | hydrocortisone butyrate |
| diflorasone diacetate | methylprednisolone acetate |
| diflucortolone valerate | mometasone furoate |
| flumethasone pivalate | triamcinolone acetonide |
| and pharmacologically effective mixtures thereof. | |

Compositions according to the invention are especially advantageous for the topical administration to the skin of human subjects of betamethasone and its derivatives such as betamethasone benzoate, betamethasone dipropionate, and betamethasone valerate. It is particularly preferred to use the valerate ester, especially in the treatment of psoriasis.

The corticosteroid active substance is preferably present in an amount of 0.01–1.0% w/w more preferably 0.05–0.2% w/w.

In view of the complexity of the composition, it has been found that unexpectedly in order to ensure stability of the active isomer of the corticosteroid in the composition and thus to ensure delivery of the most active isomer to the epidermis, it is necessary to buffer the composition by including a suitable buffering agent. Suitable buffering agents are acetic acid/sodium acetate, citric acid/sodium citrate and phosphoric acid/sodium phosphate, and it is desirable generally to buffer the composition to pH 3.0–6.0, preferably 4.0–5.0 and to this end the buffering agent may preferably be present in an amount of 0.01–1.0% w/w, more preferably 0.05–0.2% w/w. It is particularly preferred to use a citrate buffer system, more preferably anhydrous citric acid/potassium citrate, to buffer the composition to pH 4.5, when betamethasone valerate is used as the active substance; in this case citrate buffering stabilises the more active 17valerate ester over the less active 21-valerate ester in the complex composition and ensures that the most effective form of the active substance is efficiently delivered to the epidermis.

Preparation of the composition may be effected by conventional means so as to produce a homogeneous solution of fatty alcohol(s) (wax) in an alcohol/water base. The relative proportions of the fatty alcohol(s), water/aliphatic alcohol and propellant are conveniently controlled according to conventional means so as to provide a homogeneous clear solution and so as to allow the formation of a suitable quick-break foam. Generally speaking the fatty alcohol(s), surface active agent, aliphatic alcohol and humectant (if present) are preferably mixed together with the corticosteroid active substance to produce an "Alcohol Phase". An "Aqueous Phase" is preferably produced by mixing the buffering agent and water. These phases are then mixed, preferably in the final container, in the required amounts. The propellant is then added under pressure to produce the composition according to the invention.

In the case of betamethasone valerate, for example, it is particularly preferred to use a composition comprising cetyl alcohol and octadecan-1-ol as fatty alcohols, together with Polysorbate 60 surface active agent, with purified water and ethanol as the aliphatic alcohol. The system is preferably buffered with anhydrous citric acid/potassium citrate and the propellant is preferably butane/propane. It is generally preferred to choose the proportion of the components to achieve a fixed pressure in the container of around 50–70 psi.

The composition of the present invention may be contained in and dispensed from a container capable of withstanding the pressure of the propellant gas and having an appropriate valve/nozzle for dispensing the composition as a foam under pressure. If the container is made of a metal material likely to suffer corrosion under the action of the composition, the composition may include a corrosion inhibitor as an additive. Thus, the presence of a corrosion inhibitor may be necessary if the container is made of tin plate. Suitable corrosion inhibitors include organic acid salts, preferably chosen from sorbic acid, benzoic acid, sodium benzoate and potassium sorbate. If used, the corrosion inhibitor may be present in amounts of 0.1–15% w/w, more preferably 0.1–3% w/w. In the present invention, aluminium cans are preferred as containers, particularly when utilising the above-mentioned composition for betamethasone valerate as the corticosteroid active substance; in this case there is no corrosion problem and there is no need for the inclusion of a corrosion inhibiting agent.

In use, the composition is sprayed, producing a semi-solid form (a foam or mousse) which is suitable for the topical application to the site of interest, eg the scalp when treating dermatological conditions of the scalp. On application, heat from the skin causes the mousse to break down into liquid form, thus releasing the aliphatic alcohol and corticosteroid active substance which penetrate the skin site, leaving a low amount of residue, many times lower than those obtained when delivering active substance from a cream base. This route of administration facilitates the ease of specific local application, and the composition according to the invention provides a convenient, controllable and efficient vehicle for delivering topically active corticosteroids to the skin. This gives greater physical control compared to conventional topical corticosteroid formulations, minimises rubbing of the target site and allows the alcoholic vehicle to penetrate the skin to deliver the active substance to where it will have the greatest effect.

The composition of the present invention may be used in treating skin diseases which are conventionally treated with corticosteroid active substances. Thus, the composition may be used in the treatment of, inter alia, eczema, infantile eczema, atopic dermatitis, dermatitis herpetiformis, contact dermatitis, seborrhoeic dermatitis, neurodermatitis, psoriasis and intertrigo. The composition is especially useful in the treatment of scalp psoriasis in human subjects.

The present invention will now be illustrated by means of the following non-limiting Example:

EXAMPLE

Betamethasone valerate composition

A betamethasone valerate formulation having the following composition was prepared:

|                          | % w/w  |
|--------------------------|--------|
| Betamethasone Valerate   | 0.12   |
| Cetyl Alcohol BP         | 1.10   |
| Octadecan-1-ol BP        | 0.50   |
| Polysorbate 60 BP        | 0.40   |
| Ethanol                  | 57.79  |
| Purified Water           | 33.69  |
| Propylene Glycol BP      | 2.00   |
| Citric Acid Anhydrous BP | 0.073  |
| Potassium Citrate        | 0.027  |
| Butane/Propane           | 4.30   |
|                          | 100.00 |

Cetyl alcohol (HYFATOL 1698, Efkay Chemicals Limited, London), octadecan-1-ol (HYFATOL 1898, Efkay Chemicals Limited, London), Polysorbate 60 (CRILLET 3, Croda Chemicals, North Humberside) and ethanol in the correct proportions were mixed and heated to about 45° C., with continuous stirring until the mix became clear. Betamethasone valerate BP (Roussel Uclaf, Virtolaye, France) was slowly transferred into the mix, again with continuous stirring until the mix became clear. (Alcoholic Phase)

Purified water was separately heated to 45° C. and anhydrous citric acid BP and potassium citrate BP transferred to the water, with continuous stirring until dissolved. (Aqueous Phase)

The Alcoholic and Aqueous phases were each filtered through 75 micron screens and the required weights filled into a can (aluminium, epoxy lined) at room temperature. After attaching a valve, the butane/propane propellant (Propellant P70) was added to the mix in the can to the required weight, and an actuator added to the valve.

The composition, on being sprayed from the can onto the skin, produces a thermophobic foam which breaks down under heating from the skin to release the active to the epidermis. The presence of the citrate buffer stabilizes the 17-valerate configuration of the betamethasone valerate over the less active 21-valerate configuration, thus producing a composition which efficaciously delivers active to the epidermis and which is particularly suitable for the treatment of psoriasis, especially scalp psoriasis.

What is claimed is:

1. A method of treating a skin disease susceptible to treatment with corticosteroid active substances, said method comprising administering topically to a patient in need thereof, an effective amount of a foamable pharmaceutical composition comprising a corticosteroid active substance, a quick-break foaming agent that comprises an aliphatic alcohol, water, a fatty alcohol and a surface active agent; a propellant; and a buffering agent present in an amount sufficient to provide a pH within the range of 3.0 to 6.0.

2. The method according to claim 1 wherein the skin disease is selected from the group consisting of eczema, infantile eczema, atopic dermatitis, dermatitis herpetiformis, contact dermatitis, seborrheic dermatitis, neurodermatitis, psoriasis and intertrigo.

3. The method according to claim 2 for treating scalp psoriasis in human subjects.

4. A method of treating a skin disease susceptible to treatment with corticosteroid active substances, said method comprising administering topically to a patient in need thereof an effective amount of a foamable pharmaceutical composition comprised of a quick-break foaming agent that comprises an aliphatic alcohol, water, a fatty alcohol and a surface active agent a propellant; an active isomer of an isomeric corticosteroid active substance; and an amount of a buffering agent effective to stabilize the active isomer against isomerization to a less active isomer.

5. The method according to claim 1, further characterized in that the amount of the corticosteroid active substance is from 0.01 to 1.0% w/w of the composition.

6. The method according to claim 1, further characterized in that the corticosteroid active substance is a topically effective corticosteroid selected from alclometasone dipropionate, amcinonide, beclamethasone dipropionate, betamethiasone benzoate, betamethasone dipropionate, betamethasone valerate, budesonide, clobetasol propionate, clobetasone butyrate, desonide, desoxymethasone, diflorasone diacetate, diflucortolone valerate, flumethasone pivalate, fluclorolone acetonide, fluocinolone acetonide, fluocinonide, fluocortin butyl, fluocortolone preparations, fluprednidene acetate, flurandrenolone, halcinonide, hydrocortisone, hydrocortisone acetate, hydrocortisone butyrate, methylprednisolone acetate, mometasone furoate, triamcinolone acetonide, and pharmacologically effective mixtures thereof.

7. The method according to claim 6, further characterized in that the corticosteroid active substance is betamethasone valerate.

8. The method according to claim 1, further characterized in that the aliphatic alcohol component is selected from the group consisting of methanol, ethanol, isopropyl alcohol, butyl alcohol, and mixtures thereof.

9. The method according to claim 8, further characterized in that the aliphatic alcohol component is ethanol.

10. The method according to claim 1, further characterized in that the fatty alcohol component is selected from cetyl, stearyl, lauryl, myristyl, and palmityl alcohols, and mixtures thereof.

11. The method according to claim 10, further characterized in that the fatty alcohol component is a mixture of cetyl alcohol and stearyl alcohol.

12. The method according to claim 1, further characterized in that the surface active agent is selected from the group consisting of ethoxylated sorbitan stearate, ethoxylated sorbitan palmitate, ethoxylated sorbitan oleate, nonyl phenol ethoxylates, fatty alcohol ethoxylates, and mixtures thereof.

13. The method according to claim 1, further characterized in that the buffering agent is selected from the group consisting of a citrate buffer, an acetic acid/sodium acetate buffer and a phosphoric acid/sodium phosphate buffer.

14. The method according to claim 13, further characterized in that the buffering agent is a citrate buffer.

15. The method according to claim 1, further characterized in that the foamable pharmaceutical composition comprises:

|                          | % w/w   |
|--------------------------|---------|
| Betamethasone Valerate   | 0.120   |
| Cetyl Alcohol BP         | 1.100   |
| Octadecan-1-ol BP        | 0.500   |
| Polysorbate 60 BP        | 0.400   |
| Ethanol                  | 57.790  |
| Purified Water           | 33.690  |
| Propylene Glycol BP      | 2.000   |
| Citric Acid Anhydrous BP | 0.073   |
| Potassium Citrate        | 0.027   |
| Butane/Propane           | 4.300   |
|                          | 100.000.|

* * * * *